(12) United States Patent
Troosters et al.

(10) Patent No.: US 8,426,735 B2
(45) Date of Patent: Apr. 23, 2013

(54) STRETCHABLE CONDUCTOR AND METHOD FOR PRODUCING THE SAME

(75) Inventors: Michel Troosters, Dion-Valmont (BE); Stephane Befahy, Brussels (BE); Sami Yunus, Namur (BE); Patrick Bertrand, Louvain-la-Neuve (BE)

(73) Assignee: Neurotech, Louvain-la-Neuve ( * ) Notice: Subject to any disclaimer, the term of this patent is extended or adjusted under 35 U.S.C. 154(b) by 395 days.

(21) Appl. No.: 12/594,400

(22) PCT Filed: Apr. 2, 2007

(86) PCT No.: PCT/EP2007/053159
§ 371 (c)(1),
(2), (4) Date: Oct. 2, 2009

(87) PCT Pub. No.: WO2008/119387
PCT Pub. Date: Oct. 9, 2008

(65) Prior Publication Data
US 2010/0089616 A1    Apr. 15, 2010

(51) Int. Cl.
*H01B 5/14* (2006.01)
(52) U.S. Cl.
USPC .................................................. 174/126.4

(58) Field of Classification Search ............ 174/126.4, 174/102 SP, 105 R; 333/237
See application file for complete search history.

(56) References Cited

U.S. PATENT DOCUMENTS

| 5,191,173 | A | * | 3/1993 | Sizer et al. ............... 174/105 R |
| 5,291,164 | A | * | 3/1994 | Levisse ....................... 333/237 |
| 5,529,829 | A | * | 6/1996 | Koskenmaki et al. ......... 428/167 |
| 5,705,967 | A | * | 1/1998 | Pirard ........................... 333/237 |
| 6,238,429 | B1 | | 5/2001 | Markowitz et al. |
| 6,976,881 | B2 | * | 12/2005 | Brunker et al. ............... 439/637 |

FOREIGN PATENT DOCUMENTS

| JP | 57-021103 | * | 3/1982 |
| JP | 09-185913 | * | 7/1997 |
| WO | WO 94/07565 | | 4/1994 |
| WO | WO 02/00292 | | 1/2002 |

\* cited by examiner

*Primary Examiner* — Chau Nguyen
(74) *Attorney, Agent, or Firm* — Christopher Casieri

(57) ABSTRACT

The present invention relates to a compliant deformable conductor and a method for producing the same, comprising a wire or a tube made of an electrically insulating material and one or more electrical leads applied on said wire or tube, wherein one or more of said leads comprise a plurality of islets of conductive material, forming an electrically conductive layer providing electrical conduction and/or electrical percolation.

7 Claims, 8 Drawing Sheets

STRETCHABLE CONDUCTOR AND METHOD FOR PRODUCING THE SAME

This application is a 371 application of PCT/EP2007/053159, filed Apr. 2, 2007.

TECHNICAL FIELD

The invention relates to the field of stretchable conductors. More particularly, it relates to the field of such conductors for implantable applications.

DESCRIPTION OF RELATED ART

Nowadays, there are several applications wherein electrically stretchable conductors are required. Applications of such conductors include implantable medical devices, and also flexible displays, wearable electronic clothing, smart skin, and sensors. Currently, in such devices as defibrillators, pacemakers or electrical stimulation systems, implantable in the body of a human, all the electrical connections are provided by using conducting wires. Therefore, it is essential that such conductors have a high degree of flexibility and compliance in order to mitigate all possible movements, as well as a low electrical resistivity. However, despite significant developments over rigid devices, current flexible conducting wires are not able to largely deform (e.g. compressing, elongating, twisting and bending) and to fully conform to their surroundings, due to the inability of metals to stretch substantially.

PRIOR ART DISCUSSION

Currently, conductive rubbers, i.e. silicone rubber filled with silver or carbon particles, are stretchable conductors that are mechanically elastic and electrically conductive. Nevertheless, they have a very high electrical resistivity that considerably changes if subjected to stretching.

Another kind of stretchable conductor is typically manufactured by arranging one or more layers of conductive material in a helical shape around an insulating support, wherein the conductive material is, for example, titanium or platinum, and the insulating support is a suitable biocompatible material such as silicone rubber.

However, the traditional method of arranging layers of conductive material on an insulating support is performed by simply depositing a continuous form of conductive material along the length of the support. This fact is relevant for the conductivity of such a conductor. In fact, when it is expanded by stretching, beyond 10%-20%, fractures occur in said layers of conductive material modifying the structure in such a way that the electrical conductance is not maintained. Therefore, the presence of such fractures produces an important loss of conductivity.

It is known from document US2006/0206185 an implantable conducting lead suitable for electrical stimulations applications, such as cochlear implants. This conducting lead comprises essentially a plurality of metallic wires extending through an insulating body in helically wound arrangement. Each of the metallic wire is made up of a plurality of separate electrical conductors. However, this conducting lead does not reveal a good degree of flexibility due to the presence of said plurality of separate electrical conductors.

Documents WO83/04182 and US2004/0055776 disclose, respectively, a body implantable lead and a stretchable conducting lead, both suitable for human implantation, such as pacemakers and cochlear implants. However, they do not resolve the above discussed drawback, revealing a low degree of flexibility and conductivity.

It is an object of the present invention to provide a stretchable conductor and method for producing the same which has a higher degree of flexibility, compliance and conductivity, in contrast with prior art conductors.

SUMMARY OF THE INVENTION

According to a first aspect of the present invention, a compliant deformable conductor is provided, such a conductor comprising a wire or a tube made of an electrically insulating material and one or more electrical leads applied on said wire or tube, characterized in that one or more of said leads comprise a plurality of islets of conductive material, forming an electrically conductive layer providing electrical conduction and/or electrical percolation.

Preferably, said one or more leads are helically wound around said wire or tube.

Advantageously, said wire or tube has a section having a diameter comprised between 50 μm and 1 cm.

More advantageously, said one or more layers of conductive material have a thickness comprised between 25 nm and 50 μm.

Preferably, said elastic material is an elastomer selected from the group comprising silicone rubber, polyurethane, neoprene, polyisoprene, polypropylene, etc.

Preferably, said conductive material is selected from the group comprising metals and conductive polymers.

In another preferred embodiment, according to the first aspect of the present invention, the conductor comprises an additional layer of insulating material around said wire or tube and said one or more leads.

In a variant of this embodiment, according to the first aspect of the invention, the conductor comprises on said additional layer of insulating material a plurality of levels made up of one or more of same leads, each level being separated by another layer of insulating material.

According to a second aspect of the present invention, a method for producing a compliant deformable conductor is provided, the method characterized in that it comprises the steps of:

a. providing a wire or tube of an elastic material, said wire or tube having a longitudinal axis;
 b. applying a twisting on said wire or tube around the axis thereof, and/or an elongation on said wire or tube along the axis thereof;
    while keeping step b:
 c. depositing one or more layers of conductive material on said wire or tube from one or more sectors along said axis;
 d. releasing said torsion and/or said elongation of said wire or tube.

Preferably, according to this second aspect of the invention, said elastic material is an elastomer selected from the group comprising silicone rubber, polyurethane and neoprene.

Advantageously, said conductive material is selected from the group comprising metals, conductive polymers and semiconductors.

According to a second embodiment, the method may also comprise the step of:

depositing an additional layer of insulating material around said wire or tube and said one or more layers of conductive materials.

More advantageously, the method may also comprises the step of providing on said additional layer of insulating material a plurality of levels made up of one or more electrical leads, each level being separated by another layer of insulating material.

According to this second aspect of the invention, this method advantageously comprises the steps of performing one or more surface preparations, before the deposition step such as removal of oligomers, activation of the surface, deposition of a thin layer of transition metal such as Titanium (Ti) or Chromium (Cr).

More preferably, said deposition of one or more layers of conductive material is performed by a physical or a chemical deposition, therefore, for example: magnetron plasma sputtering, vapor deposition, electrolytic or auto-catalytic deposition.

According to a third aspect of this invention, a multi-conductor is provided, the multi-conductor being characterized in that it comprises a plurality of conductors according to any of the embodiments or variants of the first or second aspect of this invention.

Advantageously, said plurality of conductors are embedded in a sheet or a bulk of soft material.

More advantageously, said plurality of conductors are twisted together forming a cable to be used in implantable electrodes, e.g. cuff-electrodes or DBS electrodes or in stand-alone or embedded in sheets or bulk of soft material.

According to a fourth aspect, the invention covers the use of a compliant deformable conductor according to any of the embodiments or variants of the first or second or third aspect for making a connection between implantable electrodes and an electronic device.

Preferably, said connection is realized via a connecting method selected from the group comprising wire-wrapping, conductive gluing, welding or crimping.

BRIEF DESCRIPTION OF THE DRAWINGS

FIG. 6b represents a sectional view of the conductor according to a variant of the embodiment of the invention illustrated in FIG. 6a.

DETAILED DESCRIPTION OF THE INVENTION

Figure 1:
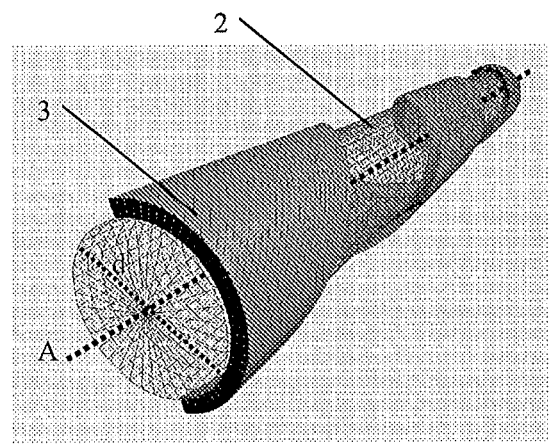
FIG. 1 illustrates a compliant deformable conductor according to a preferred embodiment of the present the invention

A compliant deformable conductor, according to a preferred embodiment of the present invention, is illustrated in FIG. 1. The conductor 1 mainly comprises a wire 2 made of an electrically insulating material and an electrical lead 3 which is helically wound around the length of said wire 2, as described hereinafter. The wire 2 is made of a deformable material, such as an elastomer, e.g. silicone rubber, polyurethane, neoprene, polyisoprene, polypropylene, etc., and has a diameter d of approximately 300 µm. The electrical lead 3 is a 100 nm thick conductive material, such as metals or conductive polymers, which is biocompatible in order to be implanted in a human body.

Figure 2A:
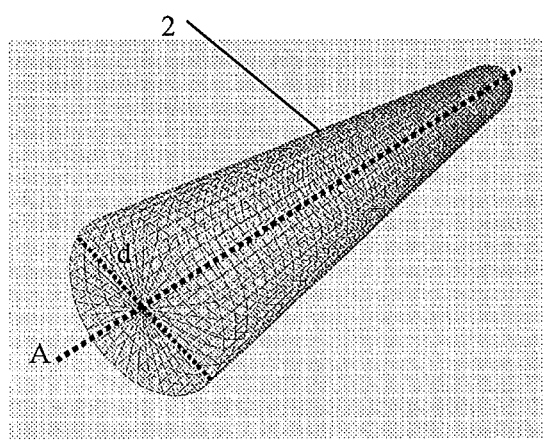
FIG. 2a, FIG. 2b and FIG. 2c, illustrate the manufacturing steps for obtaining the conductor of FIG. 1.
Figure 2B:
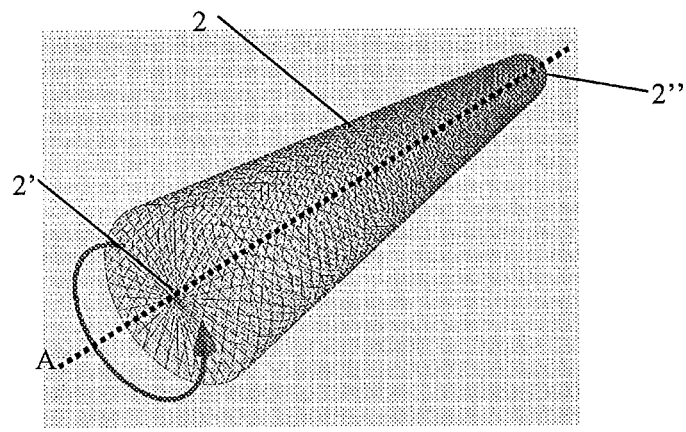
Figure 2C:
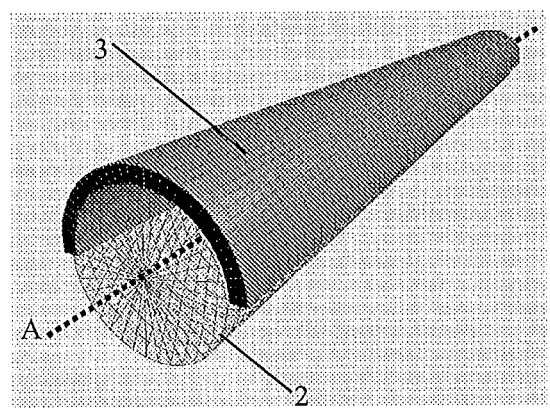
Figure 2D:
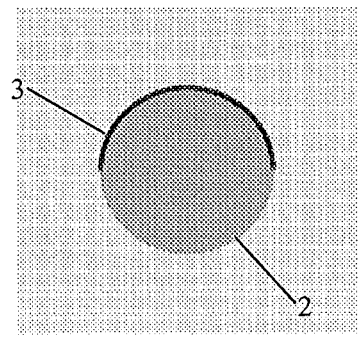
FIG. 2d is a sectional view of the conductor of FIG. 2c.

The manufacturing process for obtaining the conductor 1, according to a preferred embodiment of the present invention, comprises four successive steps that are described as follows. The first step of this process comprises providing a wire 2 made of an electrically insulating material, for example silicone rubber, with a desired length of 100 mm and a diameter of 300 µm, and having a longitudinal axis A, as shown in FIG. 2a. In the second step of this process, a twisting around axis A up to 30 turns is applied to an extremity 2' of said wire 2, while keeping in a fixed position the other extremity 2", as shown in FIG. 2b. The third step of this process essentially comprises keeping the wire 2 fixed with 25% elongation, i.e. without releasing said twisting and in applying an electrical lead 3, made up of 5 nm thick titanium (Ti) and 95 nm thick platinum (Pt), by means of well-known in the art techniques such as physical vapor deposition or chemical vapor deposition (e.g. magnetron plasma sputtering, vapor deposition, electrolytic or auto-catalytic deposition) along the surface of one side of said wire 2, as illustrated in the perspective view of FIG. 2c or in the sectional view of FIG. 2d. The fourth step of the process comprises releasing the twisting and elongation applied to the wire 2 that allows the electrical lead 3 to be helically wound around the wire 2, as shown again in FIG. 1. The pitch of such a helix is about 3 mm.

It is evident that such a device for performing the steps of this process is easy to be conceived by a man skilled in the art, therefore, as a consequence, its description is not provided, as it is not critical for the invention.

It is also evident for a man skilled in the art that whether the second step of the process produces a deformation so that some parts of the wire 2 are off-axis, i.e. the wire 2 is not in a straight position, then it is possible to apply, together with said twisting, also an elongation along the same axis, in order to keep the wire 2 in a straight position.

In a variant of this preferred embodiment, the twisting of the second step of the process might be omitted while maintaining or not the elongation along the longitudinal axis A, in order to provide a conductor 1 wherein the lead 3 is simply applied on one side of the surface thereof, i.e. helically wound around the wire 2 with an infinite pitch. In another variant, the electrical lead may be applied all over the entire surface of wire 2, i.e. helically wound around wire 2 with a zero pitch.

Figure 3:
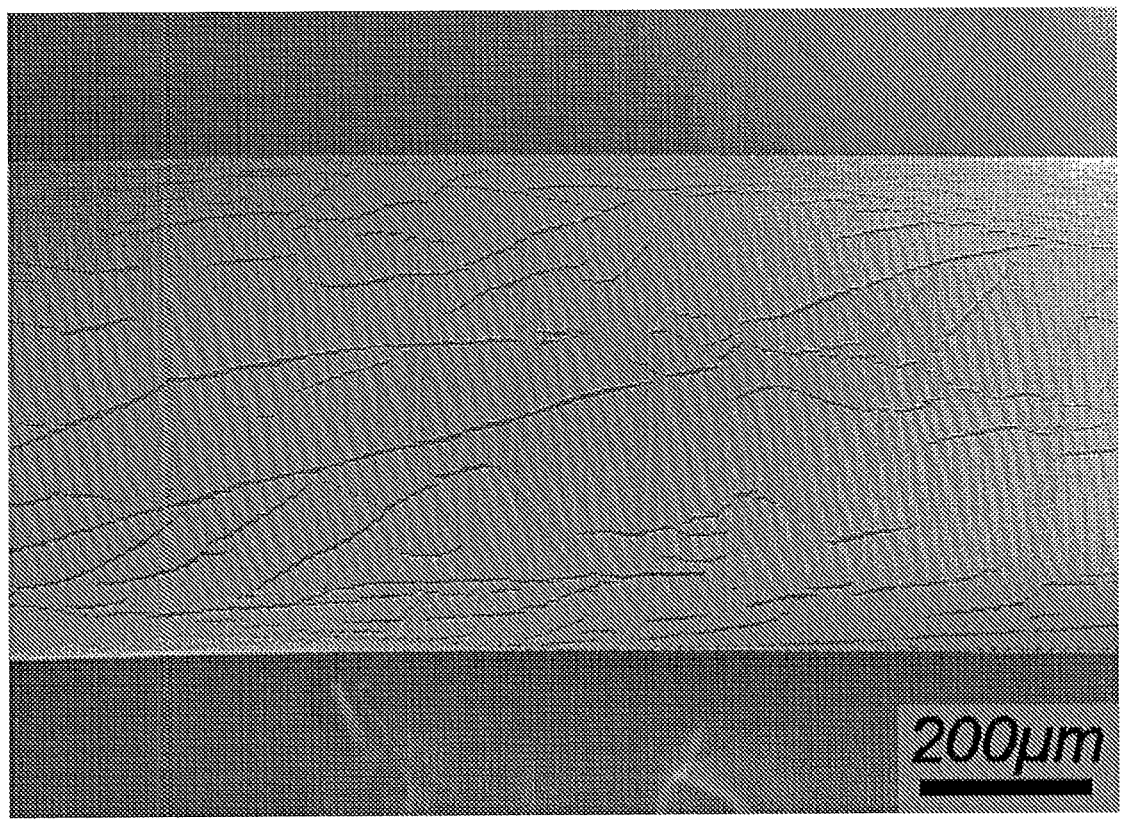
FIG. 3 and FIG. 4 show, respectively, a micrograph of a portion of the surface of the conductor of FIG. 1 and a zoomed top-view micrograph of the same portion.
Figure 4:
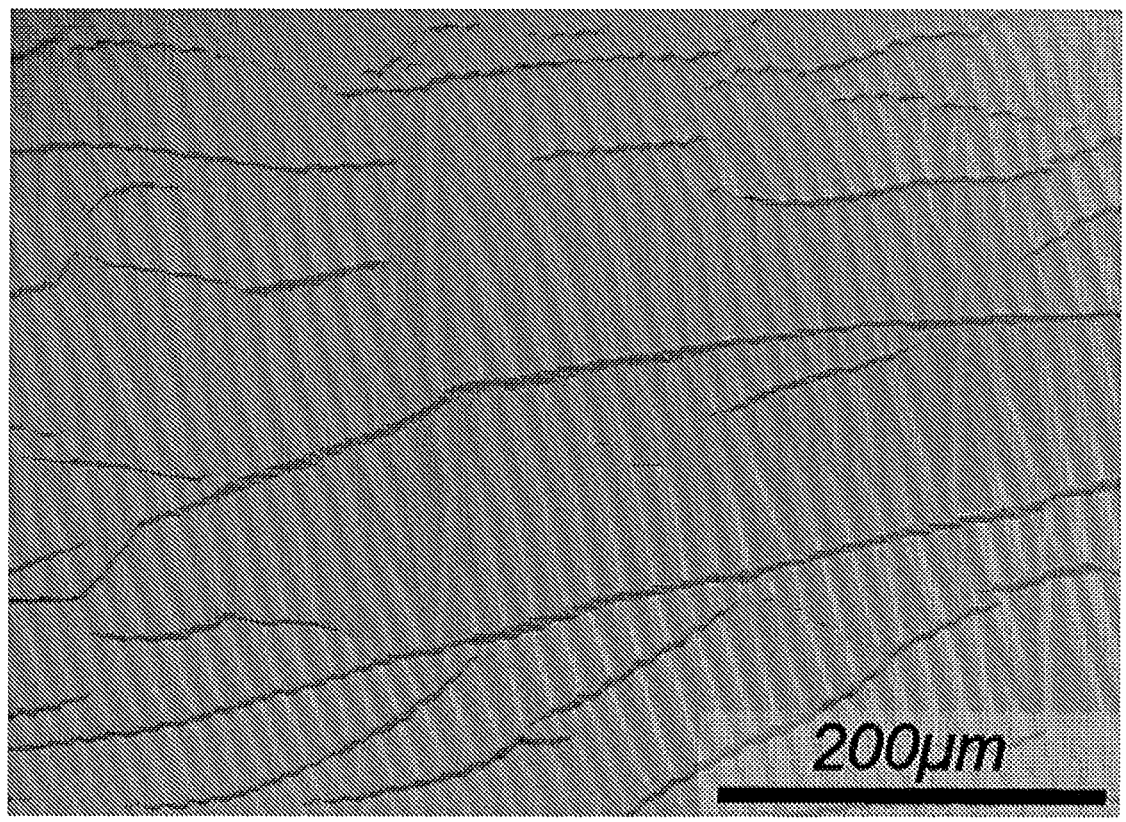

At the end of the above-described manufacture process, by referring to FIG. 3 and FIG. 4 one can observe along a portion of the conductor 1 a network of metallic fragments formed along the entire surface of the lead 3. This network comprises a plurality of randomly arranged metallic fragments or small islets of conductive material between which there are micro-cracks that are micrometer size, Y-shaped and not connected to each other. In fact, when the twisting and the elongation are released, the wire 2 contracts. Due to compressive stress, buckling in one direction of the metallic surface of lead 3 is generated. Simultaneously, due to Poisson effect, the metallic surface expands in another direction, causing tensile stress, and appearance of micro-cracks. Such a network forms a so-called "electrical percolation network", wherein electrical conductivity occurs through multiple paths, passing through individual islets and/or contact points between islets, since cracks never extend through the entire lead surface. The presence of such a percolation network allows the structure of the electrical lead 3 to maintain the electrical conductance even if the conductor 1 is subjected to extension by stretching beyond 20%. There are two main reasons that explain the maintaining of the conductance even when repeated deformations are applied to the conductor 1. On the one hand the fact that the wire 2 is extremely compliant and on the other hand the fact that this micro-crack pattern allows the conductor material deposited on the surface of this wire 2 to deform without losing its conductivity. Therefore, even when a large stretch is applied, only small and elastic strains are induced in the conductor material and all islets are induced to re-establish electrical contacts. As a consequence, since the cracks growth along surface is limited, then finite and reproducible electrical conduction is kept over repeated deformations. Relevant documents concerning this phenomenon are, for example: "Tunneling and percolation in metal-insulator composite materials", D. Toker and al., Physical review B 68, 041403 (R), 2003; and "Mechanism of reversible stretchability of thin metal films on elastomeric substrates", S. Lacour and al., Applied Physics letters 88, 204103, 2006.

Figure 5:
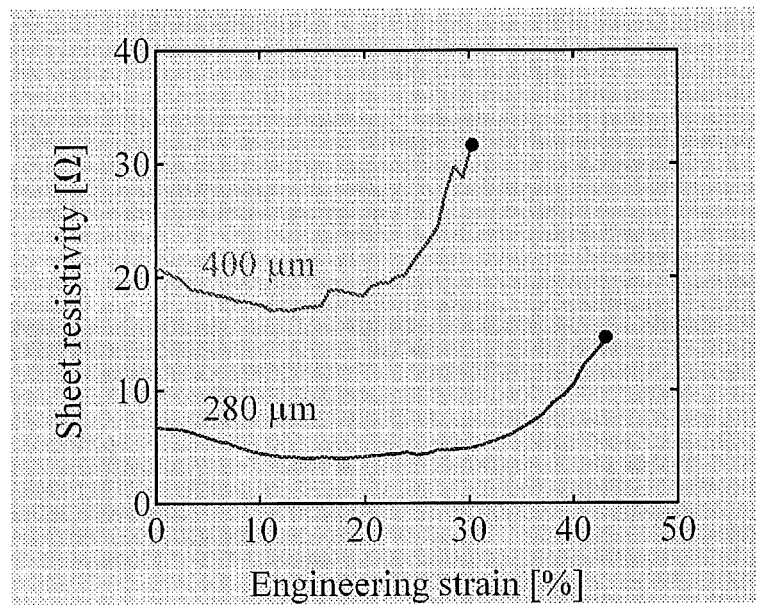
FIG. 5 represents the variation of the sheet resistivity as a function of the engineering strain for 280 µm and 400 µm radius wires; electrical failures are represented by dot marks.

Referring to FIG. 3 and FIG. 4, silicone wires of 90 mm long (L), obtained from Dow Corning Sylgard® 184, were twisted by imposing 20 full rotations ($n_r$) and stretched up to 25% of elongation ($\lambda_z$), as schematized in FIGS. 2a and 2b. The wires, still under deformation, were then exposed to an oxygen RF cold plasma. After oxidation, a gold layer was deposited by e-beam evaporation on half the wire surface. Upon release, the metallic track took an helical shape, as shown in FIG. 1. Samples having a radius of 280 μm and 400 μm were produced. The variation of the electrical resistivity upon extension is measured up to electrical failure. The sheet resistivity, $R_S$, is evaluated using:

$$R_S = R \times W_T / L_T \quad (1)$$

where R, $W_T$ and $L_T$ are the measured resistance, the metallic track width and length, respectively. These two last are estimated using $$W_T = \pi \times r \text{ and} \quad (2)$$

$$L_T = n_r \sqrt{(n_r/L)^2 + (2\pi r)^2} \quad (3)$$

where r, L and $n_r$ are the wire radius, length and the applied number of full rotations, respectively. FIG. 5 shows the typical variation of the sheet resistivity, $R_S$, as a function of the wire extension for both the 280 and the 400 μm radius samples described above. These experiments were performed three times to check reproducibility. As observed in FIG. 5, the thickest wire is the most resistive although its track width is the largest and the thinnest wire is electrically the most stable upon stretching. Electrical failure occurs at an engineering strain of 43% for the 280 μm and 30% for the 400 μm radius sample, which correspond to logarithmic strains of 0.38 and 0.27, respectively. Finally, it can be observed that for both samples, the resistivity presents a minimum that occurs at about 13% of extension (0.12 in logarithmic strain) for the 280 μm and between 15 and 18% of extension (0.13 and 0.17) for the 400 μm radius sample. It should be noted that, after electrical failure, the relaxed samples are still conductive but with an electrical resistivity about thirty percent higher.

The wire morphology is studied by Scanning Electron Microscopy (SEM) before testing for both the 280 μm (FIG. 3 and FIG. 4) and 400 μm (not shown) radius wires. The micrographs are taken in released configuration. FIG. 3 represents the full width of the wire, from the metalized side. The helix is oriented from the bottom right of the figure to the upper left. As observed in FIG. 3 showing a large metallized region and in FIG. 4 at a higher magnification, the helix surface buckles, giving rise to a regular wavelet morphology with a period of approximately 15 μm. The waves are parallel and form a 75° angle with the wire longitudinal axis. At some locations, large cracks are present in the metallic layer. However, the electrical conductivity is maintained owing to a conductive percolation network. Most of these cracks are perpendicular to the wavelets. The perpendicular cracks are also the longest and the most open. The 400 μm radius wire involves a slightly larger density of micro cracks than the 280 μm radius sample.

The better electrical behavior of the 280 μm radius sample seems a paradox owing that the metallized surface is smaller than for the 400 μm radius wire. This observation can however be explained by the smaller amount of cracks. If the cracking pattern is more dominant, conduction through percolation decreases. Regarding the minima of the curves displayed in FIG. 5, two antagonist effects probably act on the sheet resistivity during a tensile experiment: the metallic elements move apart in the extension direction but become closer in the perpendicular direction. This analysis tends to show that, for a given radius, the parameters k and $\lambda_z$ can be adjusted to find an optimal compromise between increasing the total strain in the direction of the cylinder to improve stretchability by buckling, and decreasing the strain to limit the amount of cracks. The fabrication process described in this paper (k=$n_r/L_0$=222.22 m$^{-1}$ and $\lambda_z$=$L/L_0$=1.25) seems to be a better compromise for the 280 μm wire radius, as its conductivity only starts deteriorating at an extension close to the imposed prestretch of 0.4. A smaller prestretch should lead to smaller stretchability. Concerning the 400 μm wire case, the amount of cracks is over the optimum.

In a variant of this preferred embodiment, the extremity 2", instead of being fixed, is also twisted around the longitudinal axis of the wire 2, in the opposite direction with respect to the extremity 2'.

Figure 6A:
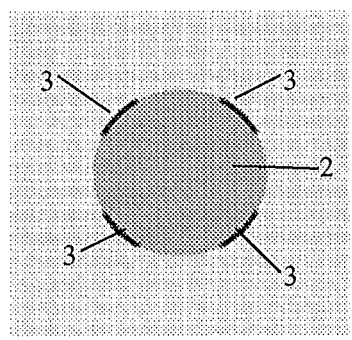
FIG. 6a represents a sectional view of the conductor according to another embodiment of the invention.

According to a second embodiment of the present invention, as illustrated in FIG. 6a, the conductor 1 is made up of four electrical leads 3 that are helically wound around the wire 2 following the same process as above described. However the numbers of electrical leads can vary as desired and depends on the particular application.

Figure 6B:
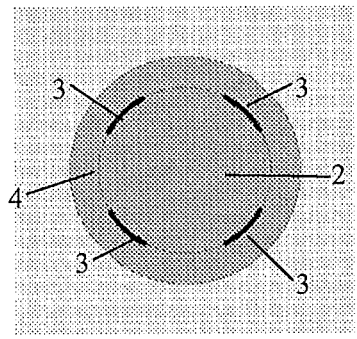

In a variant of this second embodiment of the invention and as illustrated in FIG. 6b, the conductor 1 also comprises an insulating biocompatible material 4 covering electrical leads 3 and the wire 2. This insulating material 4 is used in order to insulate the electrical leads 3 and prevent contact between the electrical leads 3 and the environment.

Figure 6C:
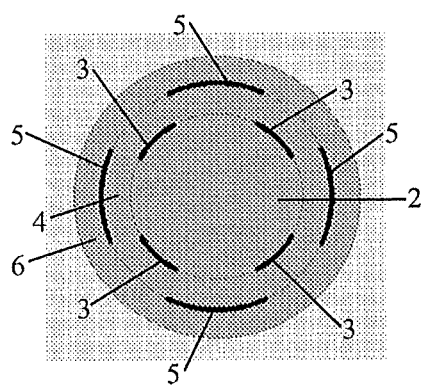
FIG. 6c represents a sectional view of the conductor according to another embodiment of the invention.

In another variant of this second embodiment, as illustrated in FIG. 6c, the conductor 1 additionally comprises a second level of four electrical leads 5 helically wounded around this first insulating material 4 (covering electrical lead 3 and wire 2) and a second insulating material 6 covering this second level of four electrical leads 5.

Figure 7:
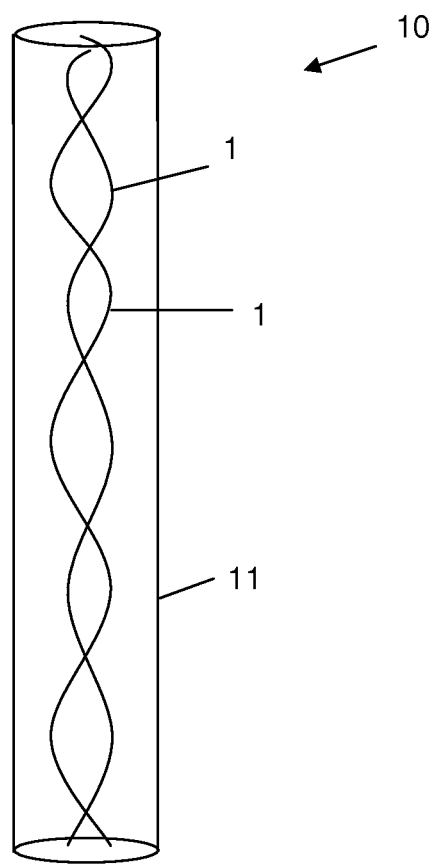
FIG. 7 represents a multi-conductor comprising a plurality of conductors according to the invention.

According to a third embodiment of the invention, as illustrated in FIG. 7, the conductor 1 may be used in order to form a multi-conductor 10 wherein a certain number of same conductors as conductor 1 are bounded together or twisted together as to form a cable, for example to be embedded in a sheet or a bulk of soft material 11.

In conclusion, highly compliant and stretchable three dimensional metallic helixes on silicone wire substrate can be very simply processed by twisting and stretching the wire before the metal deposition. Upon release, the metallic track deforms to a helix whose surface is wavy and cracked. The wavelets and cracks orientation are function of three parameters: the wire radius, the imposed rotations divided by the length of the cylinder and the superimposed stretching in the direction of the longitudinal cylinder axis. Electrical resistivity at rest and under stretching can be optimized by imposing predeformation allowing to increase the amount of surface buckling while limiting the amount of cracks.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated. In particular, the wire 2, represented as having a circular section, may have other shapes, such as a square or may be hollow, i.e. a tube. Furthermore, the dimensions given in the above description may vary depending on the needs of the application, therefore, for example the diameter of wire 2 may vary between 50 μm and 1 cm, the thickness of the electrical lead between 25 nm and 50 μm, or the pitch of the helix may vary between 0; +∞[, and so on . . . .

The invention claimed is:

1. A method for producing a stretchable conductor comprising the steps of:
    a. providing a wire or tube of an elastic material, said wire or tube having a longitudinal axis;
    b. applying a twisting on said wire or tube around the axis thereof, and/or an elongation on said wire or tube along the axis thereof;
    while maintaining step b:
    c. depositing one or more layers of conductive material on said wire or tube from one or more sectors along said axis; and,
    d. releasing said torsion and/or said elongation of said wire or tube.

2. The method of claim 1, wherein said elastic material is an elastomer selected from the group consisting of silicone rubber, polyurethane and neoprene.

3. The method of claim 1, wherein said conductive material is selected from the group consisting of metals and conductive polymers.

4. The method of claim 1, further comprising the step of:
    depositing an additional layer of insulating material around said wire or tube and said one or more layers of conductive materials.

5. The method of claim 4, further comprising the step of providing on said additional layer of insulating material a plurality of levels made up of one or more electrical leads, each level being separated by another layer of insulating material.

6. The method of claim 1, further comprising the steps of performing one or more surface preparations, before the deposition step said surface preparation being selected from the group consisting of removal of oligomers, activation of the surface and deposition of a thin layer of a transition metal.

7. The method of claim 1, wherein said deposition of one or more layers of conductive material is performed by physical or chemical deposition.

* * * * *